000
United States Patent [19]

Allgeier et al.

[11] 3,948,931

[45] Apr. 6, 1976

[54] TRIAZOLO BENZODIAZEPINE-1-CARBOXAMIDES

[75] Inventors: Hans Allgeier, Haagen, Germany; André Gagneux, Basel, Switzerland

[73] Assignee: Ciba-Geigy Corporation, Ardsley, N.Y.

[22] Filed: Nov. 21, 1973

[21] Appl. No.: 418,137

[30] Foreign Application Priority Data

Nov. 28, 1972 Switzerland.................... 17300/72

[52] U.S. Cl. 260/308 R; 260/239 BD; 260/247.2 A; 260/268 TR; 260/293.59; 260/561 H; 424/250; 424/267; 424/269

[51] Int. Cl.² .................................... C07D 487/04

[58] Field of Search ................... 260/308 R

[56] References Cited

UNITED STATES PATENTS 3,562,251  2/1971  Fryer et al..................... 260/239 BD
3,701,782  10/1972  Hester........................... 260/308 R
3,759,943  9/1973  Hester........................... 260/308 R

*Primary Examiner*—Alton D. Rollins
*Attorney, Agent, or Firm*—Joseph G. Kolodny; John J. Maitner; Theodore O. Groeger

[57] ABSTRACT

Compounds of the class of 6-phenyl-4H-s-triazolo[4,3-a][1,4]benzodiazepine-1-carboxamides, their 5-oxides and their pharmaceutically acceptable acid addition salts have valuable pharmacological properties and are active ingredients for therapeutic compositions. In particular, these new compounds have an anti-convulsive and anti-aggressive action and potentiate the action of anaesthetics. Specific embodiments are N,N-dimethyl-6-phenyl-8-chloro-4H-s-triazolo[4,3-a][1,4]benzodiazepine-1-carboxamide, 6-phenyl-8-chloro-4H-s-triazolo[4,3-a][1,4]benzodiazepine-1-carboxamide, N,N-dimethyl-6-(o-chlorophenyl-8-chloro-4H-s-triazolo[4,3-a][1,4]benzodiazepine-1-carboxamide and 6-(o-chlorophenyl)-8-chloro-4H-s-triazolo[4,3-a][1,4]benzodiazepine-1-carboxamide.

8 Claims, No Drawings

TRIAZOLO BENZODIAZEPINE-1-CARBOXAMIDES

DETAILED DESCRIPTION

The present invention relates to new diazepine derivatives, to therapeutical preparations containing the new compounds, and to the use thereof.

The diazepine derivatives according to the invention correspond to the general formula I

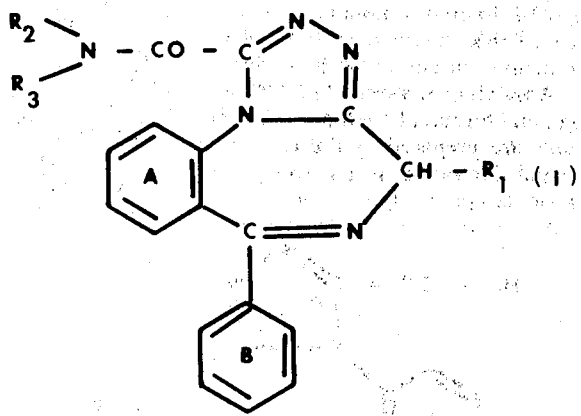

wherein $R_1$ represents hydrogen or an alkyl group having 1 to 3 carbon atoms, and $R_2$ and $R_3$ represent hydrogen, alkyl groups having 1 to 6 carbon atoms, or hydroxyalkyl groups having 2 to 6 carbon atoms, or aralkyl groups having 7 to 9 carbon atoms, whereby, when $R_2$ and $R_3$ simultaneously represent alkyl groups as aforesaid, these alkyl groups may be bound together in the β- or γ-position either direct or via an oxygen atom, the imino group, or a lower alkylimino or hydroxyalkylimino group having at most 4 carbon atoms to form a bivalent radical having in all at most 10 carbon atoms, and the rings A and B are unsubstituted or substituted by halogen up to atomic number 35, alkyl or alkoxy groups each having 1 to 6 carbon atoms, or by trifluoromethyl or nitro groups.

The invention relates also to the 5-oxides of compounds of the general formula I, and to the addition salts of compounds of the general formula I with inorganic and organic acids.

As an alkyl group in the compounds of the general formula I, $R_1$ is, for example, the methyl, ethyl or propyl group; as alkyl groups having 1 to 6 carbon atoms, $R_2$ and $R_3$ are, for example, propyl, isopropyl, butyl, isobutyl, pentyl, isopentyl or hexyl groups, and preferably methyl or ethyl groups; as hydroxyalkyl groups having at most 6 carbon atoms, they are, for example, 2-hydroxypropyl, 3-hydroxypropyl, 2-hydroxybutyl, 3-hydroxybutyl, 2-hydroxy-1-methyl-propyl, 2-hydroxypentyl, 2-hydroxyhexyl and, in particular, 2-hydroxyethyl groups; and as aralkyl groups having at most 7 to 9 carbon atoms, they are, for example, benzyl, phenethyl, α-, o-, m- or p-methylbenzyl, 3-phenylpropyl or α-methylphenethyl groups.

Alkyl groups $R_2$ and $R_3$ bound together in the β- or γ-position in the above defined manner form, together with the adjacent nitrogen atom, i.e. as a grouping $NR_2R_3$, e.g. the 1-pyrrolidinyl, piperidino, hexahydro-1H-azepin-1yl, morpholino, 1-piperazinyl or hexahydro-1H-1,4-diazepin-1-yl group. The two last-mentioned groups can be substituted in the 4-position, i.e. in the imino group e.g. by methyl, ethyl, propyl, isopropyl, butyl, isobutyl, 2-hydroxyethyl, 2-hydroxypropyl, 3-hydroxypropyl or 3-hydroxybutyl group, while all the aforementioned rings can, in addition, be substituted on carbon atoms by ethyl, propyl or, in particular, methyl groups. The following may be given as examples of C-alkyl-substituted and C- and N-substituted radicals $NR_2R_3$: the 2,5-dimethyl-1-pyrrolidinyl, 2-methyl-, 3-methyl- and 4-methyl-piperidino, 2,6-dimethyl-piperidino, 2,4,6-trimethyl-piperidino, 2,2,6,6-tetramethyl-piperidino, 2,5-dimethyl-1-piperazinyl, 2,4,5-trimethyl-1-piperazinyl, 2,4,6-trimethyl-1-piperazinyl and 3,4,5-trimethyl-1-piperazinyl groups.

Halogen atoms as substituents of rings A and B are fluorine, chlorine or bromine atoms; while alkyl groups and alkoxy groups having 1 to 6 carbon atoms are respectively, e.g. methyl, ethyl, propyl, isopropyl, butyl, isobutyl, tert.butyl, pentyl, isopentyl, 2,2-dimethylpropyl, hexyl or isohexyl groups and methoxy, ethoxy, propoxy, isopropoxy, butoxy, isobutoxy, pentyloxy, isopentyloxy, 2,2-dimethyl-propoxy, hexyloxy or isohexyloxy groups. A substituent of ring A is, in particular, in the 8-position and is preferably fluorine, bromine, the nitro group, the trifluoromethyl group and, in particular, chlorine. Ring B is preferably unsubstituted, or substituted in any position by fluorine, chlorine or bromine, the trifluoromethyl group or the nitro group, especially, however, by fluorine or chlorine in the o-position.

The compounds of the general formula I, their 5-oxides and the corresponding addition salts with inorganic and organic acids possess valuable pharmacological properties. They have a central depressant action, particularly an anticonvulsive and anti-aggressive action, and potentiate the action of anaesthetics. Their anticonvulsive activity can be demonstrated, for example, in the pentetrazole test on the mouse with oral doses of from ca. 0.5 mg/kg. The central depressant, particularly anticonvulsive, properties, as well as further properties, which can be verified by selected standard tests [cp. W. Theobald and H. A. Kunz, Arzneimittelforsch. 13, 122 (1963) and also W. Theobald et al., Arzneimittelforsch. 17, 561 (1967)], characterise the compounds of the general formula I and their 5-oxides, as well as their pharmaceutically acceptable addition salts with inorganic and organic acids, as active substances for tranquillisers and anticonvulsants, which can be used, for example, for the treatment of states of tension and agitation, as well as for the treatment of epilepsy.

Of particular importance are compounds of the general formula I in which $R_1$ is hydrogen, $R_2$ and $R_3$ each independently represent hydrogen or alkyl groups having 1 to 6 carbon atoms, preferably methyl or ethyl groups, ring A is unsubstituted or preferably substituted by a halogen atom up to atomic number 35, the nitro or trifluoromethyl group, and ring B is either unsubstituted, or substituted by one of the substituents mentioned for ring A. Particularly valuable compounds within this group of compounds are, on the one hand, those having one of the above-mentioned substituents, especially a chlorine atom, in ring A in the 8-position and, on the other hand, compounds with an unsubstituted ring B or a ring B substituted in the ortho-position by fluorine or chlorine, and, in particular, those compounds which contain hydrogen as $R_1$ and hydrogen, methyl or ethyl groups as $R_2$ and $R_3$ and combine the defined substitution characteristics for rings A and B, such as N-methyl-, N-ethyl- and N,N-diethyl-6-phenyl-8-chloro-4H-s-triazolo[4,3-a][1,4] benzodiazepine-1-carboxamide and, in particular, 6-phenyl-8-chloro-4H-s-triazolo[4,3-a][1,4] benzodiazepine-1-carboxamide and N,N-dimethyl-6-phenyl-8-chloro-4H-s-triazolo[4,3-a] [1,4]benzodiazepine-1-carboxamide, and the corresponding compounds having the 6-(o-fluorophenyl)- or 6-(o-chlorophenyl)-group in place of the phenyl group, such as 6-(o-fluorophenyl)-8-chloro-4H-s-triazolo[4,3-a][1,4]benzodiazepine-1-carboxamide, N,N-dimethyl-6-(o-chlorophenyl)-8-chloro-4H-s-triazolo [4,3-a][1,4]benzodiazepine-1carboxamide, N-methyl-, N-ethyl- and N,N-diethyl-6-(o-chlorophenyl)-8-chloro-4H-s-triazolo[4,3-a][1,4]benzodiazepine-1-carboxamide and, in particular, 6-(o-chlorophenyl)-8-chloro-4H-s-triazolo[4,3-][1,4]benzodiazepine-1-carboxamide and N,N-dimethyl-6-(o-chlorophenyl)-8-chloro-4H-s-triazolo[4,3-a][1,4]benzodiazepine-1-carboxamide.

The compounds of the general formula I, their 5-oxides and their acid addition salts are prepared according to the invention by a process in which an aldehyde of the general formula II

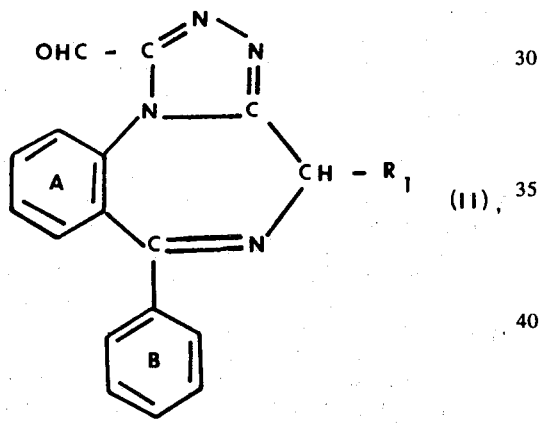

(II), wherein $R_1$ has the meaning given under formula I, and rings A and B can be substituted as defined under formula I, is reacted with a compound of the general formula III

(III), wherein $R_2$ and $R_3$ have the meanings given under formula I, in the presence of an alkali metal cyanide and of a selective oxidising agent; and, optionally, the resulting reaction product oxidised to a 5-oxide; or, optionally, converted into an addition salt with an inorganic or organic acid. The alkali metal cyanide employed is, for example, potassium cyanide and especially sodium cyanide. By selective oxidising agents are meant such ones which, under the reaction conditions, do not act on the aldehyde group of the starting material of formula II, but which are able to oxidise the hydroxymethylene group of the intermediately formed cyanohydrin to the carbonyl group. A particularly suitable oxidising agent is manganese dioxide. Preferably, the reactions with manganese dioxide are performed in isopropanol in the cold state, e.g. between $-10°$ C and $+10°$ C, preferably at $0°$ C, or in another lower secondary alkanol, to which can be added a further organic solvent inert under the reaction conditions, preferably one having a good dissolving capacity for the starting materials of the general formula II, such as, for example, dioxane. Relative to the compound of the general formula II, there are used, for example, an appreciable excess of the compound of the general formula III, the ca. 5-fold molar amount of alkali metal cyanide and the ca. 20-fold molar amount of manganese dioxide, with a reaction time of 2 to 6 hours, preferably ca. 4 hours.

According to a second process, the compounds of the general formula I, their 5-oxides and their acid addition salts are prepared by the reaction of a reactive functional derivative of a carboxylic acid of the general formula IV

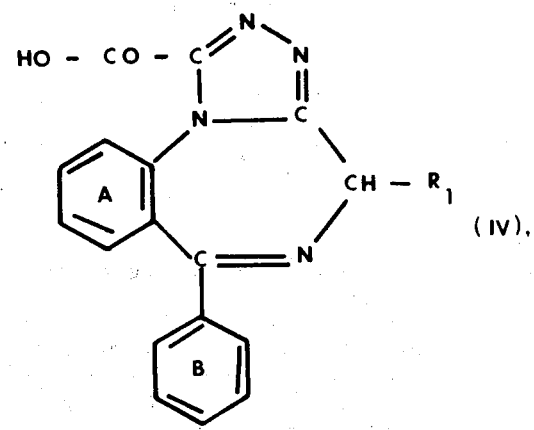

(IV), wherein $R_1$ has the meaning given under formula I and rings A and B can be substituted as defined under formula I, or of the 5-oxide of such a compound, with a compound of the previously defined general formula III in which $R_2$ and $R_3$ have the meanings given under formula I; and, optionally, the oxidation of a resulting compound of the general formula I to its 5-oxide; or the conversion thereof into an addition salt with an inorganic or organic acid. Suitable reactive functional derivatives of carboxylic acids of the general formula IV are, for example, lower alkyl esters, such as the methyl esters or ethyl esters of carboxylic acids of the general formula IV, which can be reacted at room temperature, or if necessary with heating, in the presence or absence of an inert organic solvent, such as, e.g. dioxane or tetrahydrofuran, with compounds of the general formula III to give the corresponding amides of the general formula I.

The preparation of reactive functional derivatives of carboxylic acids of the general formula IV iS described further on in the text. Compounds of the general formula III are known in considerable numbers, and others can be obtained in a manner analogous to that in the case of the known compounds.

A third process for the preparation of the new compounds of the general formula I, their 5-oxides and their acid addition salts is one in which a compound of the general formula V

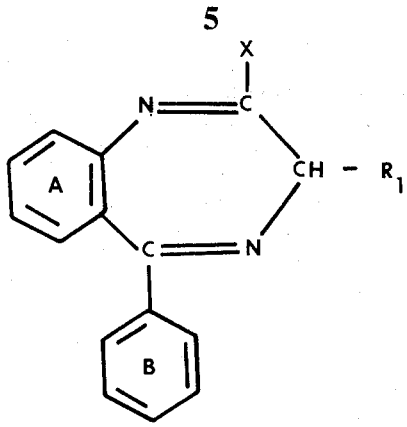

(V)

wherein
X represents the mercapto group, a lower alkoxy or alkylthio group which are optionally activated by a substituent, or an optionally mono- or di-substituted amino group,
$R_1$ has the meaning given under formula I, and rings A and B can be substituted as defined under formula I, is condensed with a compound of the general formula VI

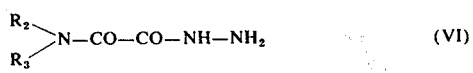

(VI)

wherein $R_2$ and $R_3$ have the meanings given under formula I; and, optionally, the reaction product obtained oxidised to its 5-oxide, or converted into an addition salt with an inorganic or organic acid.

As a lower alkylthio or alkoxy group, X is preferably the methylthio or ethylthio group or the methoxy or ethoxy group. These groups can be activated by a substituent. Such activated groups are, e.g. the o- or p-nitro-benzylthio group or the o- or p-nitrobenzyloxy group. As a mono-substituted amino group, X is, in particular, a lower alkylamino group such as the methylamino group, or an aralkylamino group such as the benzylamino group. As a disubstituted amino group, X is, in particular, a lower dialkylamino group, such as the dimethylamino group.

The reaction according to the invention is preferably performed at a reaction temperature of ca. 80° to 160° C in an inert solvent. Suitable inert solvents are, for example, hydrocarbons such as toluene or xylene, halogenated hydrocarbons such as chlorobenzene, a lower alkanol such as, e.g. ethanol, isopropanol or butanol, ethereal liquids such as diethylene glycol dimethyl ether, diethylene glycol diethyl ether or dioxane and amides, especially N,N,N,',N',N'',N''-hexamethylphosphoric acid triamide, or sulphoxides such as dimethylsulphoxide. The reaction times are between ca. 1 and 24 hours.

Starting substances embraced by the general formula V are described in the literature; see, among other references, L. H. Sternbach and E. Reeder, J. Org. Chem. 26, 1111 (1961), S. C. Bell et al., J. Med. Chem. 5, 63 (1962), G. A. Archer and L. H. Sternbach, J. Org. Chem. 29, 231 (1964) and J. Farber et al., J. Med. Chem. 7, 235 (1964). Also compounds embraced by the general formula VI are described, such as 5-methyl-semioxamazide (N-methyloxamic acid-hydrazide) by G. Tiric in Rec. trav. chim. 52, 363 (1933), 5-ethyl-semioxamazide [Zh. Obshch. Khim. 34 (1), 28–32 (1964), CA 60, 10391 d] and 5-allyl-semioxamazide [U.S. Pat. Spec. No. 2,835,703, CA 52, P 15568 f]. Further compounds of the general formulae V and VI can be prepared in a manner analogous to that for the known compounds. For example, further starting materials of of the general formula V having an optionally substituted amino group X are obtained by reduction of the corresponding 4-oxides described in the literature, and further compounds of the general formula VI, e.g. by reaction of oxamic acid methyl esters or oxamic acid ethyl esters, N-substituted according to the definition for $R_2$ and $R_3$, with hydrazine.

Compounds of the general formula I wherein $R_2$ and $R_3$ denote hydrogen atoms, while $R_1$ has the meaning given under formula I and rings A and B can be substituted as defined under formula I, their 5-oxides and their acid addition salts are prepared by a fourth process in which a nitrile of the general formula VII

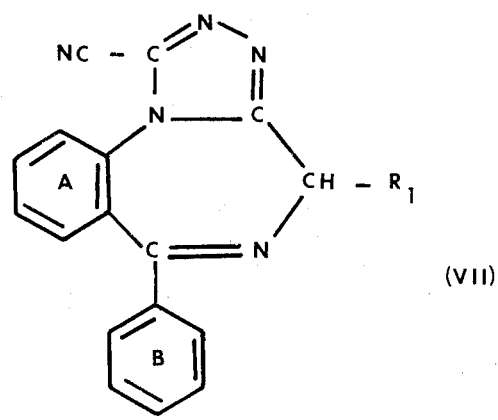

(VII)

wherein $R_1$ has the meaning given under formula I, and rings A and B can be substituted as defined under formula I, or the 5-oxide thereof, is partially hydrolysed; and optionally, a resulting compound of the general formula I oxidised to its 5-oxide; or converted into an addition salt with an inorganic or organic acid. The partial hydrolysis can be performed in an alkaline, aqueous-organic medium or in an acid aqueous or aqueous-organic medium under mild conditions, i.e., for example, at a temperature of between 0° C and room temperature or, if necessary, at slightly elevated temperature. As an alkaline medium, it is possible to use, for example, a diluted, e.g. 0.2N to 2N, alkali hydroxide solution, particularly sodium or potassium hydroxide solution, together with an organic solvent miscible with water or readily soluble in water, such as, e.g. methanol, ethanol or dioxane. The acid medium employed can be, for example, dilute sulphuric acid or hydrochloric acid in the presence or absence of organic solvents, such as, e.g. acetic acid or dioxane. The preparation of the nitriles of the general formula VII is described later on in the text.

The oxidation reaction to give the corresponding 5-oxides, which optionally follows the processes according to the invention for the preparation of compounds of the general formula I, is preferably performed by means of hydrogen peroxide or peroxy acids at a temperature of ca. 0° to 70° C. Suitable peroxy acids are, e.g. peroxyacetic acid or peroxybenzoic acids, such as peroxybenzoic acid or, in particular, m-chloroperoxybenzoic acid. The oxidising agents are preferably used in a solvent, e.g. peroxyacetic acid in acetic acid and peroxybenzoic acids in halogenated hydrocarbons, such as methylene chloride or chloroform.

The starting materials of the general formula II for the first-mentioned process for the preparation of the compounds of the general formula I can be obtained, for example, by condensation of compounds of the general formula V, of which, as already mentioned, some representatives are known, with benzoyloxyacetic acid hydrazide to corresponding 1-(benzyloxymethyl)-4-H-s-triazolo[4,3-a][1,4]benzodiazepines; splitting of these with hydrobromic acid in acetic acid to the corresponding 4H-s-triazolo[4,3-a][1,4]benzodiazepine-1-methanols; and oxidation thereof by means of manganese dioxide, e.g. in benzene, or by means of dimethylsulphoxide in the presence of dicyclohexylcarbodiimide and phosphoric acid.

As starting materials for the second-mentioned process for the preparation of compounds of the general formula I, the lower alkyl esters of carboxylic acids of the general formula IV are obtainable, for example, by reaction of an aldehyde of the general formula II with a lower alkanol, in the presence of sodium cyanide and manganese dioxide in acetic acid at room temperature.

The nitriles of the general formula VII, required as starting materials for the fourth-mentioned process, are obtained, for example, by oxidation of aldehydes of the general formula II in the presence of ammonia, with use of oxidising agents stronger than those required for the first-mentioned process for the preparation of compounds of the general formula I. Preferably, oxidation is performed with lead tetraacetate in an inert organic solvent, such as, e.g. benzene, at temperatures of between ca. 0° and 50° C, preferably at room temperature.

A further process for the preparation of nitriles of the general formula VII comprises the oxidation of corresponding compounds containing, instead of the cyano group, the aminomethyl group. Oxidation in this case too is preferably performed by means of lead tetra-acetate. Finally, reference is also made to the possibility of obtaining the nitriles of the general formula VII, widely applicable as intermediates, by dehydration of the corresponding amides embraced by the general formula I in which $R_2$ and $R_3$ denote hydrogen atoms, for example, by means of phosphorous oxychloride or phosphorus pentoxide in an organic solvent such as, e.g. dimethylformamide.

The present invention relates also to such modifications of the aforementioned processes, whereby a process is interrupted at some stage, or whereby a compound occurring as an intermediate at some stage is taken as the starting product and the uncompleted steps are performed, or whereby a starting material is formed under the reaction conditions or, optionally, is used in the form of a salt. Instead of racemates of optically active compounds, it is also possible to use as starting materials isolated optical antipodes or, in the case of disatereomeric compounds, a specific racemate. Furthermore, such starting materials can be optionally used in the form of salts.

The compounds of the general formula I which are obtained by the processes according to the invention are optionally converted in the usual manner into their addition salts with inorganic and organic acids. Acids used for salt formation are, for example, hydrochloric acid, hydrobromic acid, sulphuric acid, phosphoric acid, perchloric acid, methanesulphonic acid, ethanesulphonic acid or citric acid, preferably in the presence of a solvent, such as, e.g. acetone, methanol, ethanol or ether, or mixtures thereof.

The compounds of the general formula I, as well as their 5-oxides and the corresponding, pharmaceutically acceptable acid addition salts, are preferably administered orally or rectally. The daily doses vary between 0.02 and 2 mg/kg for warm-blooded animals. Suitable dosage units such as dragees, tablets or suppositories, preferably contain 0.5 – 50 mg of an active substance according to the invention, i.e. of a compound of the general formula I, of its 5-oxide or of a pharmaceutically acceptable acid addition salt of the former. The said dosage units are prepared by combination of the active substance with solid pulverulent carriers, such as lactose, saccharose, sorbitol or mannitol; starches such as potato starch, maize starch or amylopectin, also laminaria powder or citrus pulp powder; cellulose derivatives or gelatine, optionally with the addition of lubricants such as magnesium or calcium stearate or polyethylene glycols, to form tablets or dragee cores. The last-mentioned are coated, for example, with concentrated sugar solutions which may also contain, e.g. gum arabic, talcum and/or titanium dioxide, or with a lacquer dissolved in readily volatile organic solvents or solvent mixtures. Dyestuffs can be added to these coatings, e.g. for indentification of the various dosage amounts. Further suitable oral dosage units are hard gelatine capsules, as well as soft closed capsules made from gelatine and a softener such as glycerin. The former contain the active substance preferably as a granulate in admixture with lubricants such as talcum or magnesium stearate, and optionally stabilisers such as sodium metabisulphite or ascorbic acid.

The following examples further illustrate the preparation of tablets, dragees and suppositories:

a. 50.0 g of N,N-dimethyl-6-phenyl-8-chloro-4H-s-triazolo[4,3-a][1,4]benzodiazepine-1-carboxamide is mixed with 500 g of lactose and 292 g of potato starch; the mixture is moistened with an alcoholic solution of 8 g of gelatine, and granulated through a sieve. After drying of the granulate, 60 g of potato starch, 60 g of talcum, 10 g of magnesium stearate and 20 g of highly dispersed silicon dioxide are mixed in, and the mixture is subsequently pressed out to form 10,000 tablets each weighing 105 mg and each containing 5 mg of active substance; the tablets can optionally be provided with grooves to give a more precise adjustment of the dosage amount.

b. 2.5 g of N,N-dimethyl-6-co-chlorophenyl)-8-chloro-4H-s-triazolo[4,3-a][1,4]benzodiazepine-1-carboxamide is well mixed with 16 g of maize starch and 6 g of highly dispersed silicon dioxide. The mixture is moistened with a solution of 2 g of stearic acid, 6 g of ethylcellulose and 6 g of stearin in ca. 70 ml of isopropyl alcohol, and granulated through a sieve III (Ph. Helv. V). The granulate is dried for ca. 14 hours and subsequently passed through sieve III–IIIa. It is then mixed with 16 g of maize starch, 16 g of talcum and 2 g of magnesium stearate, and the mixture pressed out to form 1000 dragee cores. These are coated with a concentrated syrup of 2 g of lacca, 7.5 g of gum arabic, 0.15 g of colouring agent, 2 g of highly dispersed silicon dioxide, 25 g of talcum and 53.35 g of sugar, and subsequently dried. The dragees obtained each weigh 161.0 mg and each contain 1.0 mg of active substance.

c. 10 g of N,N-dimethyl-6-phenyl-8-chloro-4H-s-triazolo [4,3-a][1,4]benzodiazepine-1-carboxamide and 1990 g of finely ground suppository foundation substance (e.g. cocoa butter) are thoroughly mixed and then melted. From the melt, maintained homogeneous by stirring, are poured 1000 suppositories each weighing 2 g and each containing 10 mg of active substance.

The following examples further illustrate the preparation of the new compounds of the general formula I as well as of starting materials not hitherto known; the examples are, however, in no way intended to limit the scope of the invention. The temperature values are expressed in degrees Centigrade.

EXAMPLE 1

0.245 g (0.005 mole) of sodium cyanide is added at 0°, with stirring, to the saturated solution of ammonia in 15 ml of isopropanol. After 5 minutes, a solution of 0.322 g (0.001 mole) of 6-phenyl-8-chloro-4H-s-triazolo[4,3-a][1,4]benzodiazepine-1-carboxaldehyde in ca. 10 ml of isopropanol is added together with 0.87 g of manganese dioxide. After a further 10 minutes, another addition is made of 0.87 g (total 0.02 mole) of manganese dioxide, and the mixture stirred for 4 hours at 0°. After the addition of ca. 40 ml of methylene chloride, the reaction mixture is filtered and the filtrate concentrated by evaporation. Crystallisation of the residue from methanol/ethyl acetate/petroleum ether yields 6-phenyl-8-chloro-4H-s-triazolo[4,3-a][1,4]benzodiazepine-1-carboxamide, M.P. 285°–289°.

The starting material is prepared as follows:

a. A mixture of 1.3 g of 6-phenyl-8-chloro-4H-s-triazolo [4,3-a][1,4]benzodiazepine-1-methanol [cp., e.g. German 'Offenlegungsschrift' No. 2,156,472, Belgian Pat. No. 775,558], 3.4 g of manganese dioxide and 80 ml of benzene is refluxed for 2 hours. The reaction mixture is then filtered through a layer of silica gel, and the filtrate concentrated by evaporation. The residue is chromatographed through silica gel (Merck, 0.063 – 0.2 mm particle size) with various ethyl acetate/ethanol mixtures of increasing ethanol content as the eluant. The fractions eluted with ethyl acetate/ethanol (4:1) are combined and concentrated by evaporation. The residue is crystallised from ethyl acetate/petroleum ether to obtain 6-phenyl-8-chloro-4H-s-triazolo[4,3-a][1,4]benzodiazepine-1-carboxaldehyde, M.P. 161–163°.

EXAMPLE 2

80 ml of isopropanol is added to 120 ml of a 20% solution of dimethylamine in dioxane. After this has cooled to 0°, additions are made, with stirring, of 3.7 g (0.075 mole) of sodium cyanide and, after 5 minutes, of a solution of 4.8 g (0.015 mole) of 6-phenyl-8-chloro-4H-s-triazolo[4,3-a][1,4]benzodiazepine-1-carboxaldehyde [see Example 1 a)] in 50 ml of dioxane/isopropanol (1:1), as well as of 13 g of manganese dioxide. After 10 minutes, a further addition is made of 13 g of manganese dioxide (total 0.3 mole), and the mixture subsequently stirred for 4 hours at 0°. After the addition of methylene chloride, the reaction mixture is filtered and the filtrate concentrated by evaporation. Crystallisation of the residue from ethyl acetate/petroleum ether yields N,N-dimethyl-6-phenyl-8-chloro-4H-s-triazolo[4,3-a][1,4]benzodiazepine-1-carboxamide, M.P. 180°–181° C.

EXAMPLE 3

10 ml of a 20% solution of dimethylamine in dioxane is added at 25° to a solution of 0.705 g (0.002 mole) of 6-phenyl-8-chloro-4H-s-triazolo[4,3-a][1,4]benzodiazepine-1-carboxylic acid methyl ester in 10 ml of methanol. After 24 hours, the reaction mixture is concentrated by evaporation, and the residue crystallised from ethyl acetate/petroleum ether to obtain N,N-dimethyl-6-phenyl-8-chloro-4H-s-triazolo[4,3-a][1,4]benzodiazepine-1-carboxamide, M.P. 180°–181°.

The starting material is prepared as follows:

A mixture of 1.62 g (0.005 mole) of 6-phenyl-8-chloro-4H-s-triazolo[4,3-a][1,4]benzodiazepine-1-carboxaldehyde [cp. Example 1 a)], 20 ml of methanol, 1.225 g (0.025 mole) of sodium cyanide, 8.70 g (0.10 mole) of manganese dioxide and 0.40 g of glacial acetic acid is stirred for 16 hours at 25°. The reaction mixture is diluted with methanol, filtered through a layer of kieselguhr and the filtrate concentrated by evaporation. The residue is dissolved in methylene chloride, this solution washed with water and saturated sodium chloride solution, dried over magnesium sulphate and concentrated by evaporation. The oily residue is chromatographed on silica gel (Merck, 0.063 – 0.2 mm particle size) with ethyl acetate/methanol (9:1) as eluant. The fractions containing the desired product [$R_f$ = 0.7 in the eluant system ethyl acetate/isopropanol (7:1)] are combined, concentrated by evaporation, and the residue crystallised from ethyl acetate to obtain 6-phenyl-8-chloro-4H-s-triazolo[4,3-a][1,4]benzodiazepine-1-carboxylic acid methyl ester, M.P. 216°–217°.

EXAMPLE 4

A solution of 1.60 g (0.005 mole) of 6-phenyl-8-chloro-4H-s-triazolo[4,3-a][1,4]benzodiazepine-1-carbonitrile in a mixture of 50 ml of methanol and 50 ml of 1N sodium hydroxide solution is allowed to stand for ca. 10 minutes at 25°. The reaction mixture is then neutralised with 2N hydrochloric acid, and concentrated to about half its volume. The concentrate is extracted in methylene chloride, the organic solution washed with saturated sodium chloride solution, dried over sodium sulphate and concentrated by evaporation. The residue is crystallised from methanol/ethyl acetate/petroleum ether to obtain 6-phenyl-8-chloro-4H-s-triazolo [4,3-a][1,4benzodiazepine-1-carboxamide, M.P. 285°–289°.

The nitrile required as starting material is prepared as follows:

a. A solution of 4.8 g (0.015 mole) of 6-phenyl-8-chloro-4H-s-triazolo[4,3-a][1,4]benzodiazepine-1-carboxaldehyde [see Example 1 a)] in abs. benzene is saturated with ammonia. After cooling of the solution to 0°, an addition is made portionwise, with a light flow of ammonia gas and in the course of 45 minutes, of 14.0 g (0.030 mole) of lead tetraacetate. The reaction mixture is then stirred for a further 24 hours at 25°; it is subsequently diluted with ether and filtered through kieselguhr. The filtrate is washed with 1N hydrochloric acid, water and saturated sodium chloride solution, dried over magnesium sulphate and concentrated by evaporation. The residue is chromatographed through silica gel with the use of ethyl acetate as eluant. The fractions containing the desired nitrile [$R_f$ = 0.63 in the eluant system ethyl acetate/isopropanol (7:1)] are combined, and concentrated by evaporation. The residue is crystallised from ethyl acetate/petroleum ether to obtain 6-phenyl-8-chloro-4H-s-triazolo [4,3-a][1,4]benzodiazepine-1-carbonitrile, M.P. 191°–192°.

11

The nitrile can also be prepared in the following manner:

b. 4 ml of phosphorous oxychloride is added to a solution of 1.69 g (0.005 mole) of 6-phenyl-8-chloro-4H-s-triazolo[4,3-a] [1,4]benzodiazepine-1-carboxamide in 5 ml of dimethylformamide, and stirring maintained for 10 minutes at 80°. The reaction mixture is then poured on ice and extraced with ethylene chloride. The extract is washed with water and saturated sodium chloride solution, dried over magnesium sulphate and concentrated by evaporation. The residue is chromatographed on silica gel with the use of benzene and benzene/ethyl acetate mixtures as eluant. The fractions containing the desired nitrile [$R_f$ = 0.5 in the eluant system benzene/chloroform/ethyl acetate (4:4:2)] are combined and concentrated by evaporation. The residue is crystallised from ethyl acetate/petroleum ether to obtain 6-phenyl-8-chloro-4H-s-triazolo [4,3-a][1,4]benzodiazepine-1-carbonitrile, M.P. 191°–192°.

EXAMPLE 5

1.1 g (0.0225 mole) of sodium cyanide is added at 0°–5° with stirring to 60 ml of isopropanol saturated with ammonia. After 5 minutes, a solution of 1.61 g (0.0045 mole) of 6-(o-chlorophenyl)-8-chloro-4H-s-triazolo[4,3-a][1,4]benzodiazepine-1-carboxaldehyde in ca. 20 ml of isopropanol is added together with 3.9 g of manganese dioxide. After a further 10 minutes, an addition is made of 3.5 g of manganese dioxide (total 0.09 mole), and the mixture stirred for 4 hours at 0°–5°. After the addition of 50 ml of methylene chloride, the reaction mixture is filtered, and the filtrate concentrated by evaporation. The residue is dissolved in a little ethanol, and this solution chromatographed through ca. 80 g of silica gel (Merck, 0.063 – 0.2 mm particle size) with the use of the system ethyl acetate/ethanol (10:1) as the eluant, collecting fractions each of ca. 20 ml.

The fractions 13–16 are combined, concentrated by evaporation, and the residue recrystallised from ethyl acetate/petroleum ether to obtain 6-(o-chlorophenyl)-8-chloro-4H-s-triazolo[4,3-a][1,4]benzodiazepine-1-carboxylic acid isopropyl ester, M.P. 229°–230°.

The fractions 21–25 are likewise combined and then concentrated by evaporation; the residue is subsequently recrystallised from ethyl acetate/petroleum ether to obtain 6-(o-chlorophenyl)-8-chloro-4H-s-triazolo[4,3-a] [1,4]benzodiazepine-1-carboxamide, M.P. 226°–228°.

The starting material is prepared as follows:

a. A suspension of 1.3 g of 6-(o-chlorophenyl)-8-chloro-4H-s-triazolo[4,3-a]benzodiazepine-1-methanol and 3.4 g of manganese dioxide in 200 ml of benzene is refluxed for 2 hours. The reaction mixture is then filtered and the filtrate concentrated by evaporation. The resulting foam is dissolved in a little ethyl acetate and the solution chromatographed on ca. 60 g of silica gel (Merck, 0.063 – 0.2 mm particle size) with ethyl acetate as the eluant. Fractions each of ca. 80 ml are collected. The fractions 4–8 are combined, concentrated by evaporation, and the residue crystallised from an ethyl acetate/ether/petroleum ether mixture to obtain 6-(o-chlorophenyl)-8-chloro-4H-s-triazolo[4,3-a][1,4] benzodiazepine-1-carboxaldehyde, M.P. 182°–189°.

12

EXAMPLE 6

2 ml of a 20% solution of dimethylamine in dioxane is added to a solution of 0.050 g (0.0083 mole) of 6-(o-chlorophenyl)-8-chloro-4H-s-triazolo[4,3-a][1,4] benzodiazepine-1-carboxylic acid isopropyl ester (obtained according to Example 5) in 2 ml of methanol. After 5 hours' standing at 25°, the solution is concentrated by evaporation and the residue dissolved in a little ethyl acetate; the undissolved parts are removed by filtration, and petroleum ether added to the filtrate. The resulting product after filtration is N,N-dimethyl-6-(o-chlorophenyl)-8-chloro-4H-s-triazolo[4,3-a][1,4]benzodiazepine-1-carboxamide, M.P. 124°–134°.

What we claim is:

1. A diazepine derivative of the general formula I

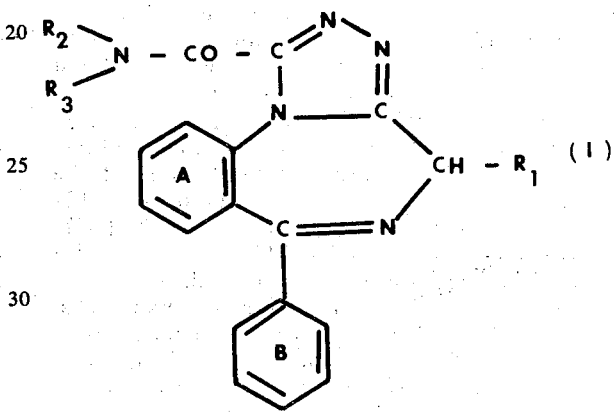

wherein $R_1$ represents hydrogen, $R_2$ and $R_3$ each independently represent hydrogen or alkyl having 1 to 6 carbon atoms, ring A is unsubstituted, or substituted in the 8-position by halogen up to atomic number 35, or trifluoromethyl or nitro, and ring B is unsubstituted, or substituted in one o-position by halogen up to atomic number 35, or by trifluoromethyl or a nitro group, their 5-oxides and their pharmaceutically acceptable acid addition salts.

2. A compound according to claim 1 having the formula I given in claim 1, in which formula $R_1$ represents hydrogen, $R_2$ and $R_3$ each independently represent hydrogen or alkyl having 1 to 6 carbon atoms, ring A is substituted in the 8-position by chlorine, and ring B is unsubstituted, or substituted in the o-position by fluorine or chlorine and their 5-oxides.

3. A compound according to claim 1 having the formula I given in claim 1, in which formula $R_1$ represents hydrogen, $R_2$ and $R_3$ each independently represent hydrogen or methyl or ethyl, ring A is unsubstituted, or substituted in the 8-position by halogen up to atomic number 35, or by trifluoromethyl or nitro, and ring B is unsubstituted, or substituted by halogen up to atomic number 35, or by trifluoromethyl or nitro and their 5-oxides.

4. A compound according to claim 1 having the formula I given in claim 1, in which formula $R_1$ represents hydrogen, $R_2$ and $R_3$ each independently represent hydrogen or methyl or ethyl, ring A is substituted in the 8-position by chlorine, and ring B is unsubstituted, or substituted in the o-position by fluorine or chlorine and their 5-oxides.

5. A compound according to claim 1, which is 6-Phenyl-8-chloro-4H-s-triazolo[4,3-a][1,4]benzodiazepine-1-carboxamide.

6. A compound according to claim 1, which is 6-(o-Chlorophenyl)-8-chloro-4H-s-triazolo[4,3-a][1,4]benzodiazepine-1-carboxamide.

7. A compound according to claim 1, which is N,N-Dimethyl-6-phenyl-8-chloro-4H-s-triazolo[4,3-a][1,4]benzodiazepine-1-carboxamide.

8. A compound according to claim 1, which is N,N-Dimethyl-6-(o-chlorophenyl)-8-chloro-4H-s-triazolo[4,3-a][1,4]benzodiazepine-1-carboxamide.

* * * * *